(12) United States Patent
Pomerantz et al.

(10) Patent No.: US 11,731,747 B2
(45) Date of Patent: Aug. 22, 2023

(54) MARINE EMISSIONS DETECTION (71) Applicant: Schlumberger Technology Corporation, Sugar Land, TX (US)

(72) Inventors: Andrew Emil Pomerantz, Lexington, MA (US); Iain Michael Cooper, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 308 days.

(21) Appl. No.: 16/904,855

(22) Filed: Jun. 18, 2020

(65) Prior Publication Data
US 2020/0398959 A1 Dec. 24, 2020

Related U.S. Application Data (60) Provisional application No. 62/863,331, filed on Jun. 19, 2019.

(51) Int. Cl.
| | |
|---|---|
| *B63G 8/00* | (2006.01) |
| *G01S 19/01* | (2010.01) |
| *G01P 13/04* | (2006.01) |
| *G01N 33/00* | (2006.01) |
| *E21B 47/001* | (2012.01) |
| *H04B 7/155* | (2006.01) |

(52) U.S. Cl.
CPC ............ *B63G 8/001* (2013.01); *E21B 47/001* (2020.05); *G01N 33/0047* (2013.01); *G01N 33/0063* (2013.01); *G01P 13/045* (2013.01); *G01S 19/01* (2013.01); *H04B 7/155* (2013.01); *B63B 2211/02* (2013.01); *B63G 2008/004* (2013.01)

(58) Field of Classification Search
CPC ..... G01V 8/02; G01W 2201/00; B63G 8/001; B63G 2008/004; E21B 47/001; G01N 33/0047; G01N 33/0063; G01P 13/045; G01S 19/01; H04B 7/155; B63B 2211/02
See application file for complete search history.

(56) References Cited

U.S. PATENT DOCUMENTS

| | | | |
|---|---|---|---|
| 9,453,828 B2 * | 9/2016 | Corbett | ................... B63B 27/30 |
| 9,638,828 B2 * | 5/2017 | Levien | .................. B64C 39/024 |
| 10,450,040 B2 | 10/2019 | Radford et al. | |

FOREIGN PATENT DOCUMENTS

EP          2273251 A2 *   1/2011   ............... G01N 1/14

OTHER PUBLICATIONS

Butz et al., 2013, Using ocean-glint scattered sunlight as a diagnostic tool for satellite remote sensing of greenhouse gases, Atmos. Meas. Tech.,6, 2509-2520—https://www.atmos-meas-tech.net/6/2509/2013/amt-6-2509-2013.pdf.

(Continued)

*Primary Examiner* — Anthony D Wiest
(74) *Attorney, Agent, or Firm* — Ashley E. Brown (57) ABSTRACT

A technique facilitates detection of gaseous emissions in a marine environment via a vessel or vessels traversing a region of the marine environment. Environmental data is collected via a detection system on each vessel and communicated to a processing system. The processing system processes various environmental data such as location data, emission detection data, wind data, and/or other data to determine an emissions result. This emissions result is output in a form to facilitate decision-making with respect to potential corrective actions to reduce the gaseous emissions.

12 Claims, 5 Drawing Sheets

(56) References Cited

OTHER PUBLICATIONS

Riddick et al., (2019) Methane Emissions from oil and gas platforms in the north sea, Atmos. Chem. Phys., 19, Issue 15, 9787-9796—https://www.atmos-chem-phys.net/19/9787/2019/.

Riddick et al., 2016, Estimating the size of a methane emission point-source at different scales: from local to landscape Atmos. Chem. Phys., (27 pages)—https://www.atmos-chem-phys.net/17/7839/2017/acp-2016-963.pdf.

Yacovitch et al., 2020, Methane Emissions from Offshore Oil and Gas Platforms in the Gulf of Mexico, Environmental Science & Tehcnology, 2020, 54, 3530-3538—https://pubs.acs.org/doi/10.1021/acs.est.9b07148?ref=pdf.

* cited by examiner

MARINE EMISSIONS DETECTION

CROSS-REFERENCE TO RELATED APPLICATION

The present document is based on and claims priority to U.S. Provisional Application Ser. No. 62/863,331, filed Jun. 19, 2019, which is incorporated herein by reference in its entirety.

BACKGROUND

Methane can be a potent greenhouse gas which potentially contributes to global warming. Some estimates suggest that 25% of global warming may result from atmospheric methane. A portion of the atmospheric methane results from methane emissions which can occur at active or abandoned oil and gas facilities. However, locating the emission source to enable reduction in the methane emissions can be problematic. Certain new technologies have been used in conjunction with aircraft and satellites to identify methane emission sources on land. However, existing technologies are limited with respect to detecting methane emissions over water and thus cannot be used to reliably identify emission sources offshore.

SUMMARY

In general, a methodology and system facilitate detection of gaseous emissions in a marine environment via a vessel or vessels traversing a region of the marine environment. Environmental data is collected via a detection system on each vessel and communicated to a processing system. The processing system processes various environmental data such as location data, emission detection data, wind data, and/or other data to determine an emissions result. This emissions result is output in a form to facilitate decision-making with respect to potential corrective actions to reduce the gaseous emissions.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a well methodology and system which facilitate detection of gaseous emissions in a marine environment via a vessel or vessels traversing a region of the marine environment. Environmental data is collected via a detection system on each vessel and communicated to a processing system. It should be noted that additional, e.g. supplemental data, may be obtained and provided to the processing system via satellites, remotely operated vehicles (ROVs), autonomous underwater vehicles (AUVs), and/or other data collection instruments and techniques. The processing system processes various environmental data such as vessel location data, emission detection data, wind data, and/or other data to determine an emissions result. The emissions result comprises relevant information on gaseous emissions, such as the level of gaseous emission and the estimated location of such emission. The emissions result is output in a form to facilitate decision-making with respect to potential corrective actions for reducing the gaseous emissions. For example, the emissions result may be output via a graphical user interface on a computer display.

Figure 1:
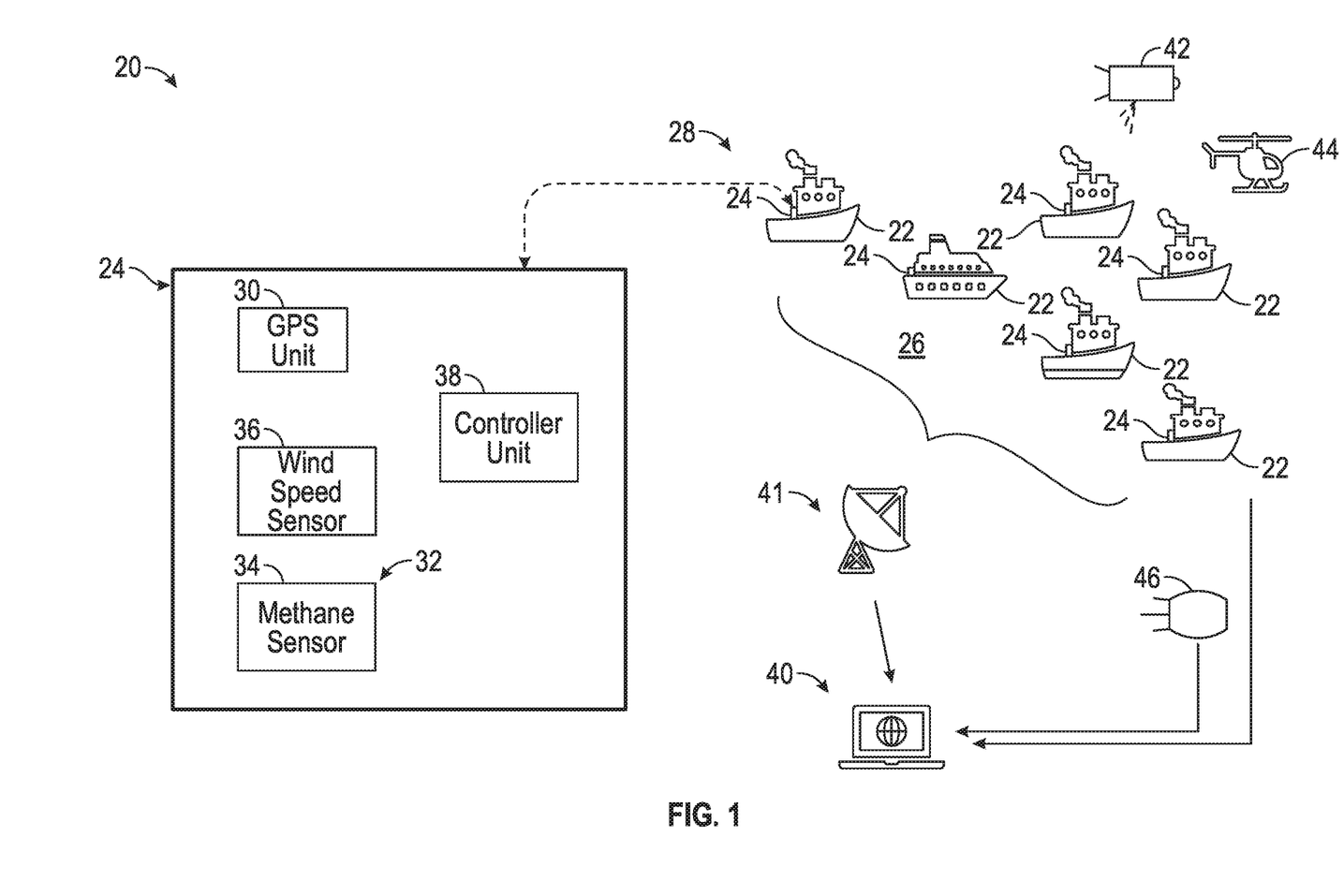
FIG. 1 is a schematic illustration of an example of various components that may be utilized in a gaseous emission monitoring and detection system, according to an embodiment of the disclosure.

Referring generally to FIG. 1, an example of a system 20 for gaseous emissions monitoring and detection is illustrated. In this example, the system 20 comprises at least one oceangoing vessel 22, e.g. a plurality of oceangoing vessels 22, which each have detection equipment 24 to detect and locate gaseous emissions, e.g. methane emissions, in a region 26 of a marine environment 28. Depending on the types of potential gaseous emissions, environment, and monitoring goals, the detection equipment 24 may comprise a variety of sensors and other components. By way of example, the detection equipment 24 on each vessel 22 may comprise a GPS unit 30 or other suitable unit to provide location data with respect to location of that specific vessel 22.

The detection equipment 24 also may comprise other sensors, such as a gaseous emission sensor 32, e.g. a methane sensor 34, to detect the presence and amount of methane and/or other gas such as ethane. Additionally, the detection equipment 24 may comprise at least one sensor 36 to facilitate locating the source of gaseous emissions. Examples of sensors 36 include sensors to detect, for example, wind speed and wind direction, e.g. anemometers, so as to facilitate determination of the origin of a specific gaseous emission. Some sensors 36 also may be in the form of current sensors to sense the speed and/or direction of ocean currents to further facilitate determination of the gaseous emission origin location. According to an embodiment, detection equipment 24 on each vessel 22 comprises at least one wind detector sensor 36, e.g. a wind speed sensor and a wind direction sensor, and at least one ocean current detector sensor 36 to monitor wind and ocean currents, respectively. The detection equipment 24 may further comprise suitable types of controller units 38 to control the collection and transfer of data from the various sensors and components of the detection equipment 24.

As the data is collected via detection equipment 24 on each vessel 22, each corresponding controller unit 38 may be used to facilitate transmission of the data to a processing system 40, e.g. a computer-based processing system. By way of example, the data transmission may be achieved by satellite transmission via a suitable satellite communication system 41. The data transmission may be conducted in real-time and/or by transmitting accumulated packets of data.

The data transmitted may include location data of each vessel 22 determined via, for example, the GPS unit 30 of each vessel 22. By collecting data from a plurality of vessels 22, the location data combined with other data, e.g. wind data, can be processed via processing system 40 according to localization algorithms to provide accurate estimates of the location of the gaseous emission, e.g. methane emission. It should be noted that the data provided by the vessel or vessels 22 may be supplemented by additional data and/or redundant data provided to processing system 40 via other sources. For example, the other sources may include at least one satellite 42 or other above surface sources, such as at least one airborne vehicle 44. Examples of airborne vehicles 44 include helicopters, planes, and lighter than air vehicles. Additional data and/or redundant data also may be provided by underwater vehicles 46, e.g. ROVs and AUVs. Embodiments of the overall system 20 may be used for a variety of marine-based emissions monitoring. The methods and apparatus described herein may be used for more accurate detection and location of gaseous emissions, e.g. methane emissions, across a marine environment.

In various embodiments, system 20 may be utilized to achieve an efficient method for identifying methane emissions from, for example, active and abandoned oil and gas facilities offshore. The methodology also can be extended for use in regions where natural seeps of methane gas are expected and also can be used to discriminate between natural (background) seeps and those from oil and gas operations. The data collected can be combined with data from appropriate sensors on subsea autonomous underwater vehicles such as the Houston Mechatronics Aquanaut which may be stationed on rigs. The combined data may be processed according to subsea plume models to determine, for example, gas concentrations and emission rates. It should be noted, however, system 20 also may be used to monitor and detect gaseous emissions of other gaseous components with suitable modifications, e.g. modifications with respect to sensor components, vessel mounting configurations, and processing calculations.

The oceangoing vessels 22 may comprise a variety of vessels, including various ships/boats such as cargo ships, supply ships, and fishing boats. Additionally, many offshore rigs have a permanently stationed boat proximate the rig for dealing with safety issues. The detection equipment 24 may be mounted to such boats so that as the boats 22 move around in the vicinity of offshore wells during their normal course of business, readings/data may be collected from the various sensors of the detection equipment 24.

If system 20 is utilized for methane emission detection and monitoring, the methane sensor 34 may comprise or may work in cooperation with various technologies useful in detecting fugitive methane emissions. Methane sensors 34 may comprise various detectors, such as sniffers and optical gas imagers, along with various permanent and mobile systems, such as point sensors open path sensors, spectrometers, lidar sensors, and/or other types of sensors which may be used to detect the presence and amount, e.g. concentration, of methane gas component.

When subsea active or abandoned oil and gas assets emit methane, the leaked gas bubbles through the water and creates an increased atmospheric concentration of methane above the location of the emitting asset. That elevated concentration can spread and move as the gas diffuses and is blown by the wind. The various sensors of detection equipment 24 provide data from each vessel 22, and this data may be used via processing system 40 to identify the approximate origin and level of the increased concentration of atmospheric methane. Based on this processing of data, the location of the emitting assets can be identified. As described in greater detail below, various algorithms, e.g. localization algorithms, may be used via processing system 40 in determining the number, location, and emissions rates of various methane emissions sources. Based on the collected data, optimization algorithms can then be used by processing system 40 to help predict where enhanced focus on future measurements and repairs are desired.

Referring again to FIG. 1, the oceangoing vessels 22 may comprise a plurality of ships traveling through the waters of the region 26 of the marine environment 28 to be investigated. Each ship comprises suitable detection equipment 24 which may include a ship position tracker such as GPS unit 30, wind/current sensor 36, e.g. a sonic anemometer, and methane sensor 34. It should be noted that data from wind type sensors 36 may be supplemented or replaced by integrating hyper local forecasting data, e.g. Dark Sky data, to aid with determining the origin of the gaseous emission. The methane sensor 34 may comprise various types of sensors, including a methane point sensor, e.g. an open path optical sensor, a cavity ringdown optical sensor, and an off-axis optical sensor (although non-optical sensors also may be used).

The oceangoing vessels 22 may comprise many types of ships or other oceangoing vessels, including oil and gas supply vessels, fishing boats, cargo ships, and/or other types of ships already present in the area. Data collection also may be supplemented with airborne vehicles 44, such as low altitude flying vehicles in the form of helicopters or drones which may be equipped with methane sensing components. Submarine vehicles 46 also can be used with suitable methane sensing components to collect emissions data.

In some applications, supplemental data may be provided by satellites 42 equipped to search for gaseous emissions. By way of example, satellites 42 may be suitably equipped to utilize glint mode for detecting emissions of certain gases such as methane. Glint mode involves the observation of sunlight which is backscattered from the Earth's surface. A glint spot on a surface of the ocean can provide a bright target and data from such targets can be used for remote sensing of atmospheric constituent concentrations (see, for example, https://www.atmos-meas-tech.net/6/2509/2013/amt-6-2509-2013.pdf).

As the oceangoing vessels 22 travel along their vessel routes during normal business, the various sensors, e.g. sensors 30, 32, 36, may be activated. The data collected from the sensors may be transmitted to the processing system 40 in real-time or in batch mode once the oceangoing vessels 22 upload their data. In some embodiments, real-time processing can be performed on one or more oceangoing vessels 22 and the data may be transmitted back to a central collection and processing system. However, the raw data also may be transmitted directly to a central processing system at a single location for processing of the data. Various combinations of on-ship processing and central processing may be utilized. In some operations, the normal travel of the oceangoing vessels 22 may be changed to facilitate performance of specific methane measurements.

Figure 2:
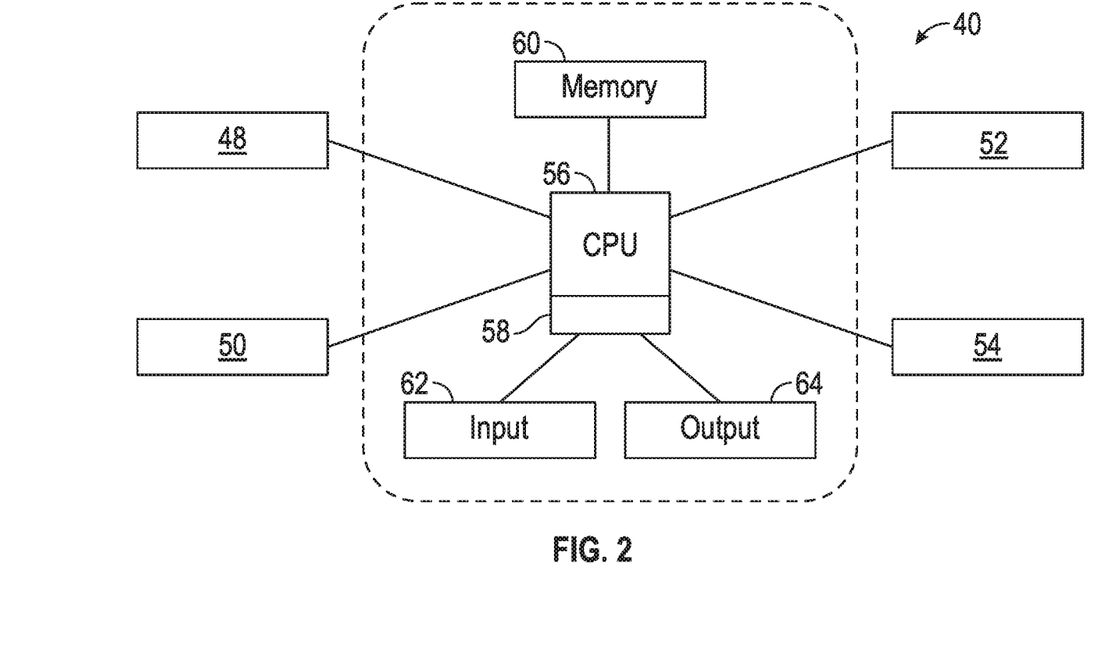
FIG. 2 is a schematic illustration of an example of a data processing system that may be used to process environmental data collected regarding potential gaseous emissions, according to an embodiment of the disclosure.

Various types of single location or multi-location processing systems 40 may be used to process the data collected from the oceangoing vessels 22 along with supplemental data which may be collected from other sources, e.g. satellites 42, aerial vehicles 44, and subsurface vehicles 46. In FIG. 2, an example of one type of processing system 40 is illustrated. According to this embodiment, processing system 40 may be a processor-based system, e.g. a computer system, which receives various types of data from the detection equipment 24 as well as other potential data collection systems.

Examples of the data collected may comprise gas component data 48 collected from the gas sensors 32/methane sensors 34. The gas component data 48 may be combined with wind and/or ocean current data 50 collected from wind/current sensors 36. The wind/current data 50 may include, for example, data on wind speed, wind direction, ocean current speed, and/or ocean current direction. The data collected via processing system 40 also may comprise vessel location data 52 provided by, for example, GPS units 30 included in the detection equipment 24 on vessels 22. Various other types of data 54, e.g. supplemental data from satellites 42, aerial vehicles 44, submarine vehicles 46, also may be accumulated and processed via processing system 40. It should be noted that other or additional gas components, e.g. ethane, may be detected. In some embodiments, methane data and ethane data may be collected to enable use of an ethane/methane ratio to determine whether a detected gas is biogenic or thermogenic. For example, the information collected can be used to determine whether methane is coming from a leaking oil/gas asset or from a natural source. Additionally, the data collected may be used to measure methane carbon-13 ($^{13}C$) and/or methane deuterium (D) isotopes, and this data may similarly be processed to determine whether the methane is biogenic or thermogenic.

In the example of FIG. 2, the processor-based system 40 is illustrated as comprising a processor 56, e.g. one or more microprocessors, which may be in the form of a central processing unit (CPU). The processor 56 is operatively employed to intake and process the different types of data 48, 50, 52, 54. Depending on the specifics of a given operation, the processor 56 may be operated to process data according to desired models/algorithms 58. By way of example, the models/algorithms 58 may comprise localization algorithms, e.g. triangulation algorithms, which are known to those of ordinary skill in the art. Localization algorithms can be used to process data from a plurality of the vessels 22 so as to accurately estimate the location of a detected gas constituent, e.g. methane resulting from a gaseous emission. Examples of models/algorithms 58 which may be employed in processing the data to detect and locate gas emissions include Gaussian plume models, Lagrangian dispersion models, reverse dispersion models, computational fluid dynamics simulations, and/or other inversion models. Further processing of, for example, wind and/or ocean current data may be used to more accurately predict the origin location of the detected gaseous emission. In some applications, the accuracy of the determination of the origin of the gaseous emission may be further improved via supplemental data from, for example, satellites 42.

As further illustrated, the processor 56 may be operatively coupled with a memory 60, an input device 62, and an output device 64. Memory 60 may be used to store many types of data, e.g. historical data and supplemental data, to facilitate processing of the data collected from the various vessels 22 and other systems. Input device 62 may comprise a variety of devices, such as a keyboard, mouse, voice recognition unit, touchscreen, other input devices, or combinations of such devices. In some applications, the input device 62 may be employed by an operator to input additional data, e.g. historical data on oil and gas production facilities. The output device 64 may comprise a visual and/or audio output device, such as a computer display, monitor, or other display medium for facilitating viewing of information via a graphical user interface. The input device 62 and output device 64 cooperate to provide an overall user interface. Additionally, the processing may be done on a single device or multiple devices at a single location or multiple locations.

Figure 3:
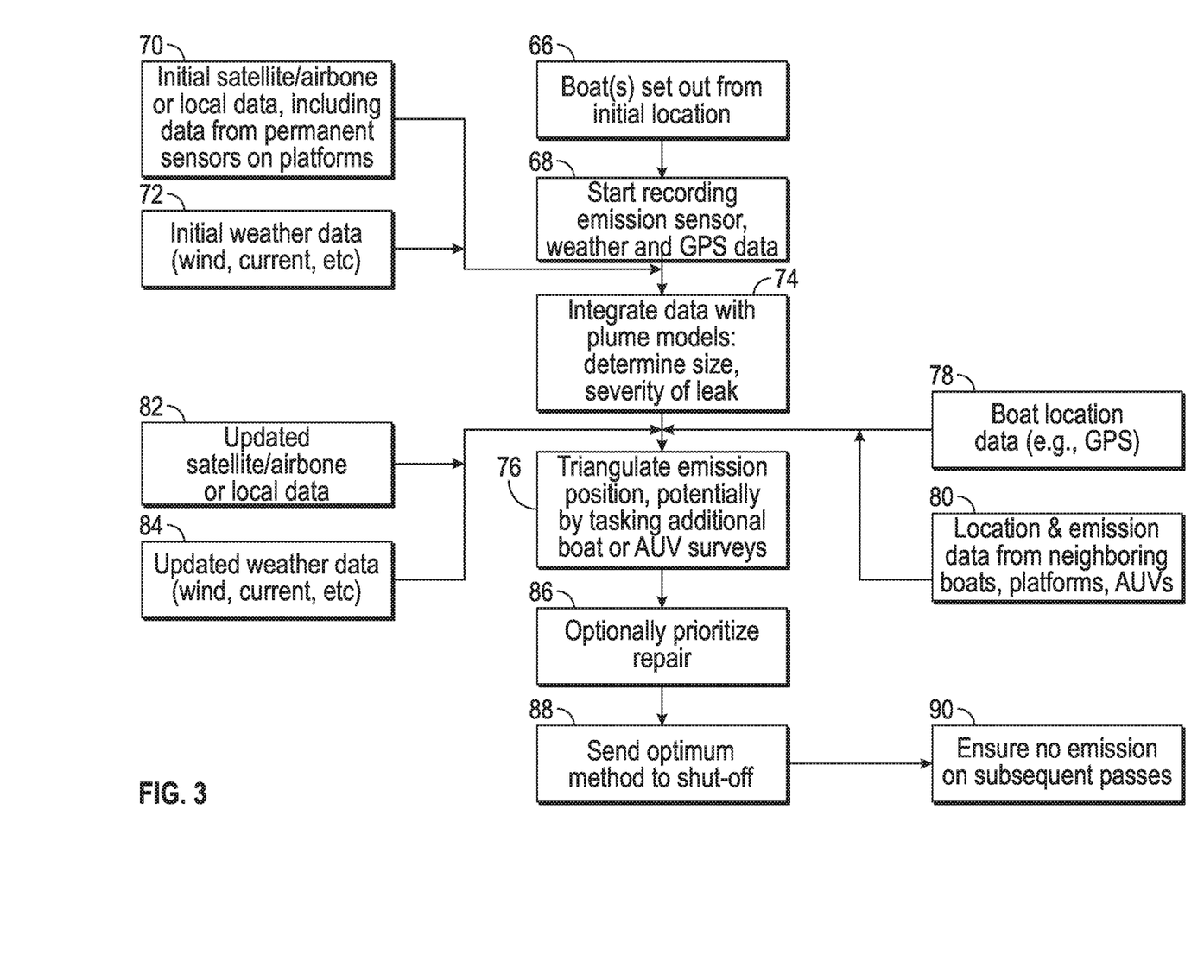
FIG. 3 is a flowchart illustrating an embodiment of a methodology for monitoring, collecting, and processing environmental data related to gaseous emissions, e.g. methane emissions, in a marine environment so as to enable corrective action, according to an embodiment of the disclosure.

Referring generally to FIG. 3, a flowchart is provided to illustrate an embodiment of a methodology for utilizing system 20 and for processing the data collected via processing system 40 so as to enable output of information which may be used, for example, to locate leaks and take corrective action. In the example illustrated in FIG. 3, vessels 22, e.g. ships, set out from an initial location, as represented by block 66, and start accumulating/recording data, as represented by block 68. The data may be obtained by suitable sensors, such as gas sensor 32, e.g. methane sensor 34, sensor 36 (e.g. wind/weather/ocean current sensor), and location/GPS sensor 30.

The recorded data may be combined with various other types of data depending on the parameters of a given application. By way of example, the recorded data may be combined with satellite data, airborne vehicle data, local data obtained from permanent sensors on platforms, and/or other data, as indicated by block 70. Initial weather data, such as wind data, ocean current data, and/or other weather data also may be combined with the recorded data, as indicated by block 72.

The combined data is provided to processing system 40 for processing and analysis via, for example, central processing unit 56. The processing system 40 may utilize a variety of models and algorithms 58 to process both the data provided initially and the ongoing recorded data. For example, the processing system 40 may be programmed with Plume models configured to integrate the data so as to determine the size and severity of a detected gaseous emission, e.g. of a given methane leak, as represented by block 74.

The location of the leak or other gaseous emission, e.g. methane emission, also may be accurately determined by utilizing localization algorithms via processing system 40, as represented by block 76. To facilitate determination of the location of the leak/emission, vessel location data 52 may be obtained via GPS sensor 30 and provided to the processing system 40, as represented by block 78. The location data from a plurality of vessels 22 may be combined with emission data 48 obtained via gas sensors 32/34 and, in some cases, with data obtained via permanent sensors and/or sensors on other vehicles such as airborne vehicles 44 and subsurface vehicles 46, as represented by block 80. As referenced above, the models/algorithms 58 used to process data 48, 50, 52, and/or 54 may comprise suitable Gaussian plume models, Lagrangian dispersion models, reverse dispersion models, computational fluid dynamics simulations, and/or other inversion models for processing the collected data so as to determine size, severity, and location of the leak.

In some applications, the data may be supplemented with, for example, location data and gas emission data from satellite-based detectors and/or airborne vehicle sensors, as represented by block 82. Of course, updated weather data, such as wind data, ocean current data, and other data related to changing weather can further be used by various localization algorithms to more accurately determine the origination location of a detected gaseous emission, as represented by block 84.

The processing system 40 is then able to output information, e.g. an alert, to an operator via output device 64. For example, the processing system 40 may output an alert to an operator when a methane emission or other gaseous emission is above a predetermined level, e.g. above a predetermined rate, concentration, and/or size. The alert also is able to provide information regarding the determined location of that emission. In some embodiments, the model/algorithms 58 also may be configured to prioritize an order of repair with respect to fixing leaks of methane (or other gaseous emissions), as represented by block 86. At this stage, an optimum approach may be determined to shut off or otherwise terminate the undesired leak/gaseous emission, as represented by block 88. Additional data may be collected via vessels 22 which remain in the area or on subsequent passes of vessels 22 to confirm reduction or elimination of the gaseous emission, as represented by block 90.

Depending on the parameters of a given operation and/or environment, the model/algorithms 58 may be adjusted to identify and locate the type and level of emission. For example, the data processing may involve identifying instances where the methane concentration reading is higher than a background level and then noting the position of the ship and the wind speed/wind direction at that time. As described above, this type of information can be input to a Plume dispersion calculation model and the data can be processed to identify and locate the methane emission. The processing may be conducted partially or wholly on a given ship or at a central processing center.

By utilizing similar information obtained from multiple vessels/ships 22 (or, in some cases, from a single vessel making multiple passes) in a given marine region 26, various localization algorithms or other suitable algorithms may be used to accurately determine a location of origination with respect to a detected gaseous emission. The utilization of oceangoing vessels 22 can be varied. Additionally, data may be collected by mounting data collection equipment 24 on a variety of ships 22 that may be passing through the given marine region 26. For example, equipment 24 may be mounted on various types of supply ships, cargo ships, fishing boats, and other ships which travel along various vessel routes through the marine region.

Figure 4:
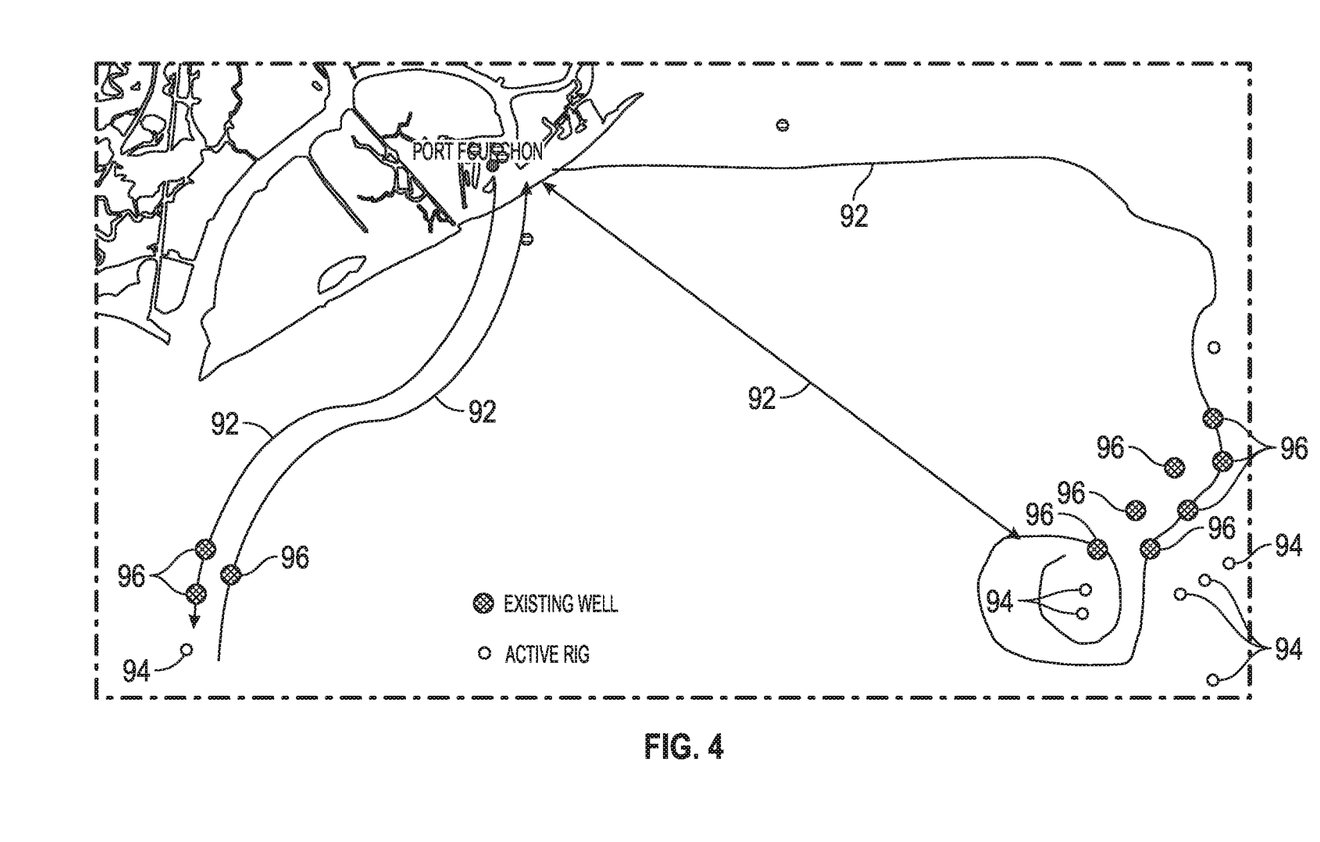
FIG. 4 is a schematic illustration of an example of potential vessel routes traveled by vessels moving through a marine environment in which gaseous emissions may occur, according to an embodiment of the disclosure.

In FIG. 4, for example, an illustration is provided which shows vessel routes 92 of ships 22 deployed in the Gulf of Mexico for supplying and serving oil and gas assets already existing in the region. FIG. 4 illustrates the vessel routes 92 relative to existing active oil/gas assets 94 and abandoned oil/gas assets 96. Vessels 22 equipped with collection equipment 24 and moving along the corresponding vessel routes 92 may be used to monitor and detect gaseous emissions in the region.

Figure 5:
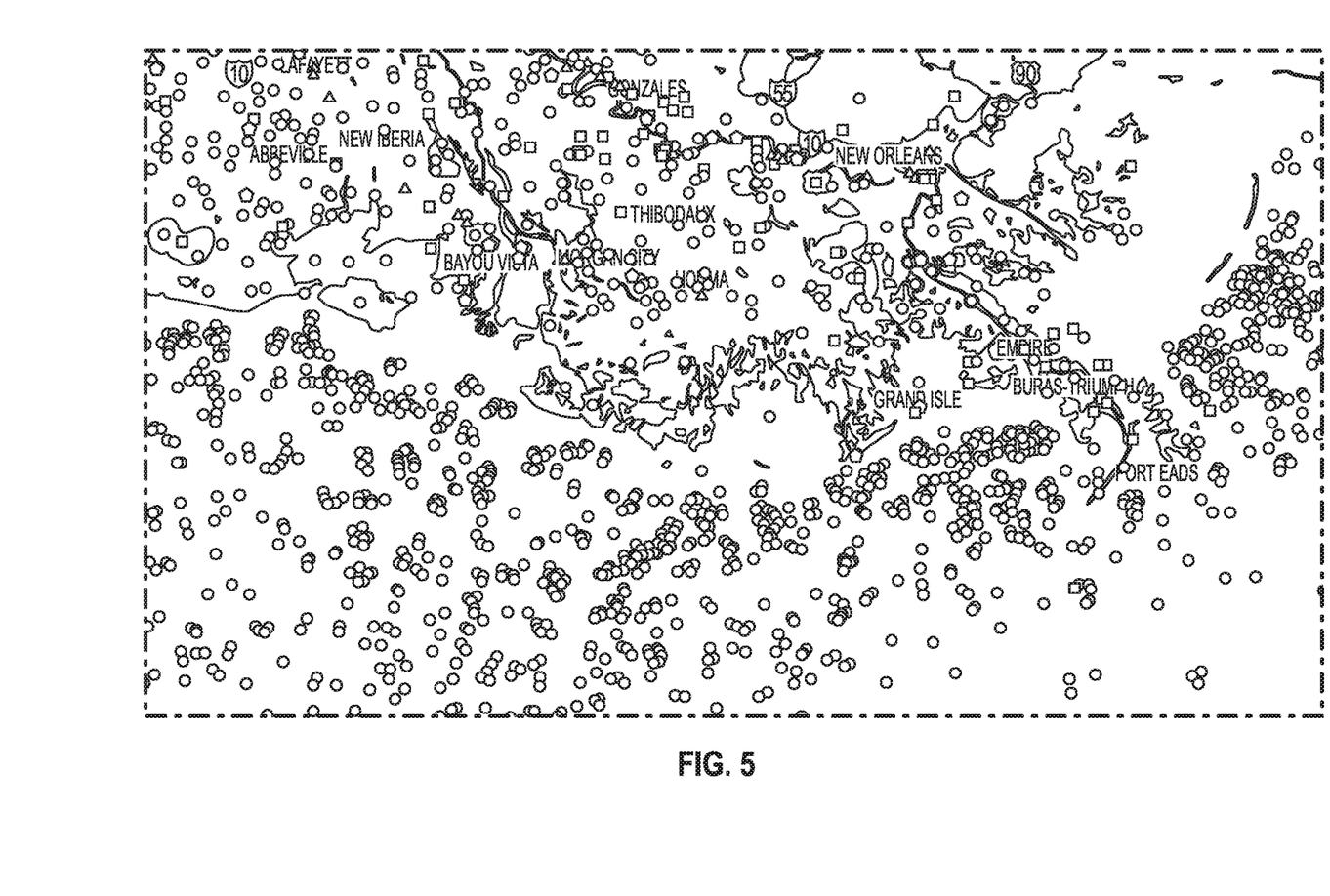
FIG. 5 is a map of an example of a marine environment which can be monitored for gaseous emissions in which the marine environment has multiple active or abandoned wells.

Referring generally to FIG. 5, a mapping of existing rigs and wells in a crowded marine region 26 is illustrated as an example of potential gaseous emission sources. By determining the vessels 22 and the vessel routes 92 through portions of this marine environment, strategic use of gaseous emission detection equipment 24 on the various vessels 22 may be employed to detect and locate methane emissions and/or other gaseous emissions. As described above, many types of supplemental data may be provided and processed to facilitate detection and location of the gaseous emissions to enable corrective actions to be taken.

In some operations, pre-planning computations may be used to pre-select the best routes and the appropriate number of routes to achieve a desired coverage of a given region 26 of a marine environment 28. For example, artificial intelligence and machine learning algorithms may be used to facilitate advantageous selection of routes and numbers of routes for detection and location of the gaseous emissions, e.g. methane leaks. The algorithms may be used continuously to develop and refine selection of routes and vessels over time.

In some environments and applications, methane leak inspection may be supplemented by using methane sensors 34 mounted on underwater vehicles 46. The data collected by the underwater vehicles 46 can be used in combination with data collected from ship mounted sensors to help guide inspection via the underwater vehicles 46. For example, data from the sensors mounted on ships 22 may be used to provide approximate locations of gaseous emission sources and to differentiate between background natural seeps and emissions from, for example, oil and gas operations. The data from the ships 22 can then be used to guide the underwater vehicles 46 to pinpoint the leak locations.

As described above, data obtained from a plurality of the ships 22 may be used in a localization algorithm to accurately determine the origination of a gaseous emission, and this determination may be used to guide the underwater vehicle or vehicles 46 to the leak location. Use of the various sensors described above enables the ongoing accumulation of information on, for example, methane concentration, wind, ship position, and ocean current information (which can affect the subsea movement of an emission plume). This data may then be used to estimate emission rates from various emission sources.

Estimates of emission rates may be used to prioritize repairs and/or to estimate emissions over larger marine regions from various emission sources. In some embodiments, data-driven approaches may be used to relate measured emissions to meta-data associated with oil/gas assets, e.g. type, size, age, and/or other suitable data associated with the oil/gas assets. Correlations in the data collected may be employed in predicting where future gaseous emissions are likely to occur so that detection efforts may be focused on a specific region or regions. This approach enables a predictive mode utilizing, for example, a database built over time to contain the meta-data associated with the oil/gas assets. Various types of statistical analysis may then be employed to provide predictions regarding the potential for leaks associated with specific assets. Based on such predictions, specific assets may be investigated for leaks via, for example, vessels 22, satellites, drones, or other suitable vehicles to obtain a higher density of sensor readings in those specific regions.

Based on the emission locations and/or the emission levels/rates of the methane or other gas measured, appropriate corrective action may be employed to repair the emissions. For example, if a given gaseous emission is above a predetermined level, an appropriate corrective action can be initiated. In some cases, the corrective action may involve sending repair crews to the leak location determined. However, AUVs 46 and other types of controller automated vehicles may be used for various leak repairs.

In many applications, automated alerts are generated by processing system 40 over output 64 based on pre-established emission rates or levels. These alerts can be used as inputs to a larger leak detection and repair (LDAR) program or to simply initiate further investigation efforts or repair activities. With respect to rigs, the alerts can be used to automatically identify a particular well or rig having an abnormally high emission level. This information can then be communicated to the rig for initiation of a manned or autonomous response. By way of example, the response may involve additional testing to identify the specific source or sources of emission and to then implement repair of that leak source. The data collected may be used to prioritize correction actions based on the severity of the emissions results determined. In some cases, the data collected may be used to direct AUVs 46 or other submarine vehicles to specific assets/locations to stop a methane leak or to perform other observational or corrective tasks.

Accordingly, the methodology described herein enables economic and efficient use of resources, e.g. a plurality of existing ships 22 traveling along vessel routes 92, to accumulate large amounts of data which can be used to accurately determine the level and location of gaseous emissions, e.g. methane leaks. The data can then be used to automatically trigger an alert and sometimes a repair/action recommendation via processing system 40. Consequently, the collection of data can be used to substantially address and reduce unwanted emission of gas throughout a given marine region.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method, comprising:
    equipping each oceangoing vessel of a plurality of oceangoing vessels with detection equipment having at least one methane detector, at least one GPS system, and at least one wind detector;
    collecting environmental data from the detection equipment on each oceangoing vessel, wherein the environmental data comprises methane detection data detected via the methane detector, location data of the oceangoing vessel determined via the GPS system, and wind detection data detected via the wind detector;
    transmitting the environmental data to a computer processing system;
    using the computer processing system to process the environmental data from the plurality of oceangoing vessels according to a localization algorithm to determine locations of methane emissions and further using the computer processing system to calculate levels of methane emissions; and
    outputting an indication via the computer processing system to alert an operator to a methane emission above a predetermined level at a determined location.

2. The method as recited in claim 1, further comprising prioritizing corrective actions based on a severity of the levels of methane emissions.

3. The method as recited in claim 1, wherein processing the environmental data further comprises processing satellite data obtained to provide supplemental data obtained via a remotely operated vehicle, an autonomous underwater vehicle, or a combination thereof regarding the emissions event.

4. The method as recited in claim 1, further comprising utilizing the data collected from the detection equipment to guide an automated underwater vehicle (AUV) to stop a leak of methane.

5. The method as recited in claim 1, wherein transmitting the data comprises transmitting the data to a central processing unit positioned at a single location.

6. The method as recited in claim 1, wherein collecting data comprises obtaining supplemental data via a remotely operated vehicle, an autonomous underwater vehicle, or a combination thereof.

7. The method as recited in claim 6, wherein obtaining the supplemental data further comprises obtaining meta-data on offshore assets and correlating that data with potential for future emissions so as to better focus gaseous emission detection efforts.

8. The method of claim 1, wherein processing the environmental data further comprises processing underwater emission data obtained via a methane sensor mounted on an underwater vehicle.

9. The method of claim 1, wherein processing the environmental data further comprises processing hyper local forecasting data to aid in determining the emission result.

10. The method of claim 1, wherein the localization algorithm comprises a Lagrangian dispersion model, a reverse dispersion model, or a computational fluid dynamics simulation.

11. A system, comprising:
    a plurality of vessels moving along a marine environment, each vessel comprising:
        a GPS system for detecting a location of the vessel;
        an emission sensor for detecting a gaseous emission; and
        a wind sensor for detecting a wind speed; and
    a computer based processing system configured to calculate an emissions result regarding the amount and origination location of the gaseous emission based, at least in part, on the location of each vessel determined by each GPS system, the gaseous emission detected by each emission sensor, and the wind speed detected by each wind sensor.

12. The system as recited in claim 11, wherein the emission sensor comprises a methane sensor.

\* \* \* \* \*